United States Patent
Davidsen

(10) Patent No.: US 6,635,019 B2
(45) Date of Patent: Oct. 21, 2003

(54) SCANHEAD ASSEMBLY FOR ULTRASONIC IMAGING HAVING AN INTEGRAL BEAMFORMER AND DEMOUNTABLE ARRAY

(75) Inventor: Richard Edward Davidsen, Everett, WA (US)

(73) Assignee: Koninklijke Philips Electronics NV, Eindhoven (NL)

( * ) Notice: Subject to any disclaimer, the term of this patent is extended or adjusted under 35 U.S.C. 154(b) by 0 days.

(21) Appl. No.: 09/682,289

(22) Filed: Aug. 14, 2001

(65) Prior Publication Data

US 2003/0036702 A1 Feb. 20, 2003

(51) Int. Cl.⁷ ................................................ A61B 8/14
(52) U.S. Cl. ...................................... 600/459; 600/437
(58) Field of Search ............................... 600/447, 459, 600/437

(56) References Cited

U.S. PATENT DOCUMENTS

| | | | |
|---|---|---|---|
| 4,437,033 A | 3/1984 | Diepers | 310/334 |
| 5,295,485 A * | 3/1994 | Shinomura et al. | 600/443 |
| 5,329,498 A | 7/1994 | Greenstein | 367/155 |
| 5,482,047 A | 1/1996 | Nordgren et al. | 128/662.03 |
| 5,617,866 A * | 4/1997 | Marian, Jr. | 439/66 |
| 5,634,466 A * | 6/1997 | Gruner | 600/136 |
| 5,817,024 A | 10/1998 | Ogle et al. | 600/447 |
| 5,820,549 A | 10/1998 | Marian, Jr. | 600/437 |
| 5,913,688 A | 6/1999 | Marian, Jr. | 439/76.1 |
| 5,964,709 A * | 10/1999 | Chiang et al. | 600/447 |
| 6,012,680 A * | 1/2000 | Edberg et al. | 244/158 R |
| 6,102,860 A * | 8/2000 | Mooney | 128/916 |
| 6,102,863 A | 8/2000 | Pflugrath et al. | 600/447 |
| 6,142,946 A * | 11/2000 | Hwang et al. | 600/459 |

* cited by examiner

*Primary Examiner*—Marvin M. Lateef
*Assistant Examiner*—William C. Jung
(74) *Attorney, Agent, or Firm*—Dorsey & Whitney LLP

(57) ABSTRACT

The present invention is directed to a scanhead having an integral beamformer and a transducer assembly that is demountable from the scanhead. The scanhead has a frontal portion including a transducer assembly, and a rear portion including a beamformer. The frontal portion further includes a connective interface to electrically communicate with a corresponding connective interface on the rear portion. In a first embodiment, the frontal portion includes an interior portion with an opening to slidably receive a corresponding portion of the rear portion. In another embodiment, an interposer is positioned between the frontal portion and the rear portion to electrically couple the spaced apart connective interfaces. In still another embodiment, the frontal and rear portions are axisymmetrically-shaped and have corresponding threaded portions to couple the frontal and rear portions.

41 Claims, 14 Drawing Sheets

SCANHEAD ASSEMBLY FOR ULTRASONIC IMAGING HAVING AN INTEGRAL BEAMFORMER AND DEMOUNTABLE ARRAY

TECHNICAL FIELD

This invention relates generally to ultrasonic diagnostic systems that use ultrasonic transducers to produce ultrasonic echoes from the interior of the body, and more particularly, to ultrasonic diagnostic systems that use scanheads having an integral beamformer and a demountable transducer array.

BACKGROUND OF INVENTION

Ultrasonic diagnostic imaging systems are in widespread use for performing ultrasonic imaging and measurements. For example, cardiologists, radiologists, and obstetricians use ultrasonic imaging systems to examine the heart, various abdominal organs, or a developing fetus, respectively. Diagnostic images are obtained from these systems by placing a scanhead against the skin of a patient, and actuating an ultrasonic transducer located within the scanhead to transmit ultrasonic energy through the skin and into the body of the patient. In response, ultrasonic echoes are reflected from the interior structure of the body, and the returning acoustic echoes are converted into electrical signals by the transducer in the scanhead.

FIG. 1 shows an ultrasonic imaging system 10 according to the prior art. A scanhead assembly 11 includes a handle portion 18 that supports a transducer assembly 16. The transducer assembly 16 is generally formed from a crystalline material, such as barium titanate or lead zirconate titanate (PZT), that is shaped to form a number of piezoelectric elements 17 capable of transmitting and receiving signals at ultrasonic frequencies. The piezoelectric elements 17 thus formed may be arranged in a linear array, or alternatively, they may be arranged in a variety of two-dimensional configurations. A scanhead cable 20 is coupled to the scanhead assembly 11 at one end, and to an ultrasonic processor 12 at the opposing end to permit the processor 12 and the scanhead assembly 11 to communicate. The ultrasonic processor 12 contains a beamformer 22 capable of exchanging signals with the scanhead assembly 11 to dynamically focus the ultrasonic signals emitted by the transducer assembly 16. Dynamic focus is achieved by controlling the relative time delays of the applied voltages on each element so that they are combined to produce a net ultrasonic signal focused at a selected point within the body being scanned. The focal point thus achieved can be moved on each successive transmitter excitation, so that the transmitted signals can be scanned across the body at various depths within the body without moving the transducer. Similar principles apply when the transducer receives a return echo from an interior region of the body. The voltages produced at the transducer elements 17 are individually delayed in time and then summed so that the net signal is dominated by the acoustic echoes reflected from a single receive focal point in the body. The dynamically focused signals may then be transferred to an image processor 24 located within the processor 12 for subsequent additional processing prior to displaying a visual image of the scanned region of the body on a visual display 14. A system controller 26 cooperatively interacts with the beamformer 22 and the image processor 24 to control the processing of the beamformed signals and the data flow from the beamformer 22.

The need for more detailed diagnostic information from ultrasound systems has progressively led to the development of systems with transducer assemblies that contain a large number of individual piezoelectric elements 17. As a result, the transducer assembly 16 may contain individual piezoelectric elements in numbers that range from a few hundred elements to as many as three thousand. Generally, each element 17 of the transducer assembly 16 must be coupled to the processor 12 by an individual coaxial line. Since all of the coaxial lines extend through the scanhead cable 20, the diameter of the scanhead cable 20 increases as the number of array elements 17 increases. Consequently, as transducer assemblies increase in size, the scanhead cable 20 becomes increasingly more difficult to manipulate during ultrasonic procedures due to decreased cable flexibility. Further, as the size and complexity of transducer arrays steadily increases, the diameter and weight of the scanhead cable 20 may become prohibitively large at some point.

In an effort to reduce the number of coaxial lines in the scanhead cable 20, prior art ultrasonic imaging systems have employed multiplexers positioned within the scanhead assembly 11 to selectively transmit and receive ultrasonic signals from the elements 17 of the transducer assembly 16. Since multiplexing permits a coaxial line to communicate with more than a single transducer element 17, the overall size of the scanhead cable 20 is reduced. Although this approach has allowed fewer coaxial lines to be used with larger array sizes, multiplexing adversely affects the aperture size, and hence the resolution of the ultrasonic imaging device since it limits the number of elements 17 that may be simultaneously active. Multiplexing may also adversely affect the frame rate of the ultrasonic imaging device.

Other prior art methods have transferred at least a portion of the signal processing from the processor 12 to the scanhead assembly 11, thus reducing the number of individual coaxial lines in the scanhead cable 20. For example, U.S. Pat. No. 6,102,863 to Pflugrath, et al. describes an ultrasonic imaging system where at least some of the beamforming processing has been moved from the processor 12 to the scanhead assembly 11. Although this approach allows an overall reduction in the number of coaxial lines in the scanhead cable, significant shortcomings still exist. For example, when it is desired to use a different transducer assembly for a particular diagnostic procedure, the scanhead assembly and the beamforming processor must both be changed since the transducer assembly is permanently coupled to the beamforming processor. Further, in the event that the transducer assembly either wholly or partially fails, the relatively costly beamforming processor might have to be discarded along with the failed transducer assembly.

Therefore, there is a critical need for a scanhead that can be coupled to an ultrasonic processor through a relatively thin cable despite having a large number of elements, and that can be replaced relatively inexpensively in the event that one or more elements fail.

SUMMARY OF INVENTION

The present invention is directed to a scanhead having an integral beamformer and a transducer assembly that is demountable from the scanhead. The scanhead has a frontal portion including a transducer assembly, and a rear portion including a beamformer. The frontal portion further includes a connective interface to electrically communicate with a corresponding connective interface on the rear portion. In one aspect of the invention, the frontal portion includes an interior portion with an opening to slidably receive a corresponding portion of the rear portion. In another aspect of the invention, an interposer is positioned between the frontal portion and the rear portion to electrically couple the spaced apart connective interfaces. In still another aspect of the invention, the frontal and rear portions are axisymmetrically-shaped and have corresponding threaded portions to couple the frontal and rear portions.

DETAILED DESCRIPTION OF THE INVENTION

The present invention is generally directed to ultrasonic diagnostic systems that use scanheads having an integral beamformer and a transducer assembly that is demountable from the scanhead. Many of the specific details of certain embodiments of the invention are set forth in the following description and in FIGS. 2 through 14 to provide a thorough understanding of such embodiments. One skilled in the art will understand, however, that the present invention may be practiced without several of the details described in the following description. Moreover, in the following description, it is understood that the mating portions of the various embodiments as herein described may be manually decoupled, so that the mating portions may be coupled and decoupled in the clinical environment without the involvement of persons with specialized skills, such as service personnel. Further, it is understood that the mating portions of the various embodiments as herein described may be coupled and decoupled without employing either commonly available or specialized tools.

Figure 1:
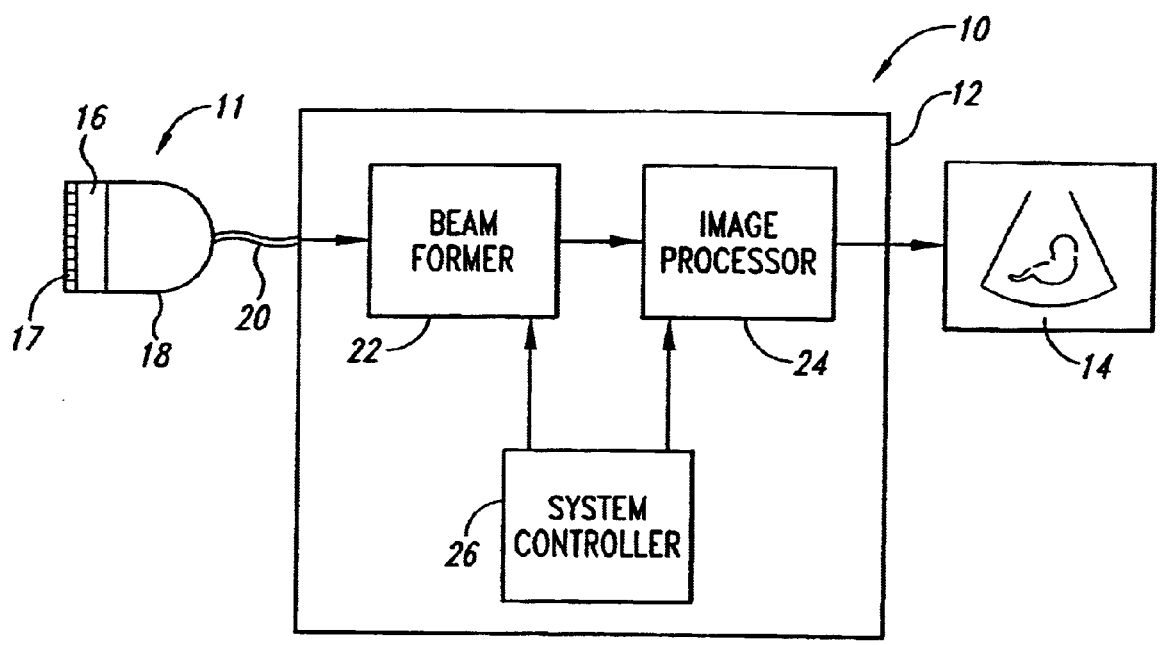
FIG. 1 is a schematic view of an ultrasonic scanhead assembly according to the prior art that is operatively coupled to ultrasonic imaging system.
Figure 2:
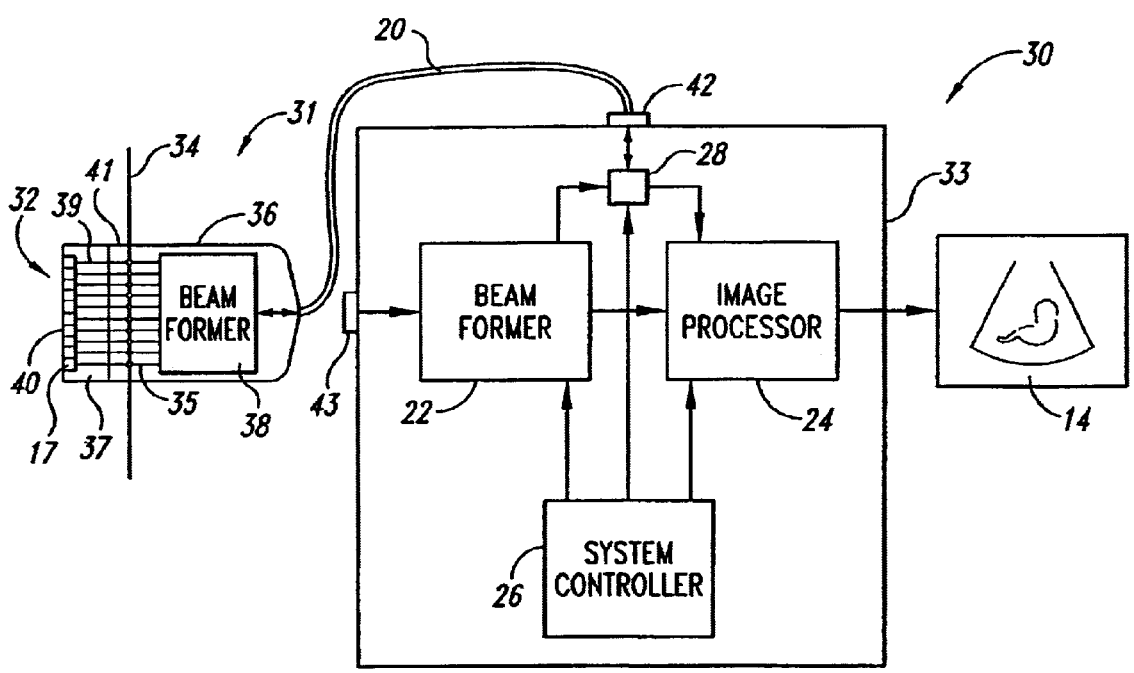
FIG. 2 is a schematic view of an ultrasonic scanhead assembly according to an embodiment of the invention that is operatively coupled to ultrasonic imaging system.

FIG. 2 is a schematic view of an ultrasonic imaging system 30 that is operatively coupled to a scanhead assembly 31 according to an embodiment of the invention. The scanhead assembly 31 is comprised of a frontal portion 41 and a rear portion 36. The frontal portion 41 includes a transducer assembly 32 that is generally formed from a bar, or block of a piezoelectric material that has been bonded to an acoustically absorbent backing layer 37 and diced to form a plurality of transducer elements 17. The transducer elements 17 may thus be arranged to form a variety of different array configurations, including linear and rectangular arrangements of the elements 17. An emission surface 40 of the assembly 32 may also be formed with a curved surface to enhance the directional characteristics of the assembly 32. The emission surface 40 may also include acoustic impedance-matching layers (not shown) and a lens (not shown). A plurality of conductors 39 project through the backing layer 37 and terminate at a connection interface 34. The rear portion 36 of the assembly 31 includes a plurality of conductors 35 that electrically couple to the plurality of conductors 39 in the frontal portion 41 when the frontal portion 41 and the rear portion 36 are mated so that a continuous electrical path is established through an interface 34.

Still referring to FIG. 2, the conductors 35 in the rear portion 36 are electrically coupled to a beamformer 38 to provide input signals to the beamformer 38. The beamformer 38 generally includes any device capable of controlling transmission, reception and processing of ultrasonic signals from the elements 17 of the array 32, so that coherent interference of the signals is attained at a particular point in a scanned region. In addition, the beamformer 38 may include any additional processing elements necessary to achieve various display modes, including, for example, a processing element to achieve B-mode (gray scale) and M-mode (motion) imaging, a color-Doppler image processing element to achieve flow imaging, or a spectral-Doppler processing element for non-imaging velocity displays. Still other processing elements may be included to achieve other display modes that are well known in the art. Moreover, a beamformer 38 that processes only a portion of the ultrasonic signals received from the array 32 is also understood to be within the scope of the present invention. The beamformer 38 may be configured to control the transducer array 32 and process signals by digital means or analog means, or by a combination of digital and analog means. For example, U.S. Pat. No. 6,102,863 to Pflugrath, et al., which is assigned to the assignee of the present invention, and is incorporated by reference, discloses analog and digital beamformers that are structured to be located within the scanhead of an ultrasonic imaging system.

A scanhead cable 20 electrically couples the scanhead assembly 31 to an ultrasonic processor 33. The scanhead cable 20 includes at least one line to transfer the analog or digital beamformed signals or data from the beamformer 38 to the processor 33. The processed information may subsequently be displayed on a visual display 14. The cable 20 also includes a line to transfer electrical power from a power supply (not shown) within the processor 33 to the scanhead assembly 31, to power the transducer array 32 and the beamformer 38. Control lines may also be included in the scanhead cable 20 to transfer control information from a system controller 26 positioned within the processor 33 to the beamformer 38.

In order to attain operability of the scanhead assembly 31 with existing processors, a switch 28 may be provided that may be manually or automatically actuated when the scanhead cable 20 is coupled to receptacle 42. The switch 28 permits the beamformer 22 located within the processor 33 to be bypassed, thus allowing the image processor 24 and system controller 26 to cooperatively interact with the beamformer 38 in the scanhead assembly 31. Conventional scanheads without an internal beamforming capability still remain useable with the processor 33 if the scanhead is coupled to receptacle 43 and switch 28 is set to enable the beamformer 22 to operate. Alternatively, the beamformer 38 may be operated in conjunction with the beamformer 22, so that a portion of the beamforming processing of ultrasonic signals occurs within the beamformer 38, with the remaining portion being processed by the beamformer 22. The partial processing of ultrasonic signals in the beamformer 38 would thus allow the number of independent signal lines contained within the scanhead cable 20 to be significantly reduced.

The ultrasonic imaging system 10 thus advantageously allows a relatively thin scanhead cable to be employed with larger transducer arrays, since the beamforming signal processing occurs at least partially in the scanhead assembly. The system also advantageously permits a variety of transducer arrays to be fitted to the scanhead assembly, thus allowing transducer assemblies of different shapes and sizes to be conveniently and removably coupled to a single beamformer portion in the scanhead. An additional feature stemming from the removability of the transducer assembly is the ability to replace defective transducer assemblies without replacing the entire scanhead assembly.

Figure 3:
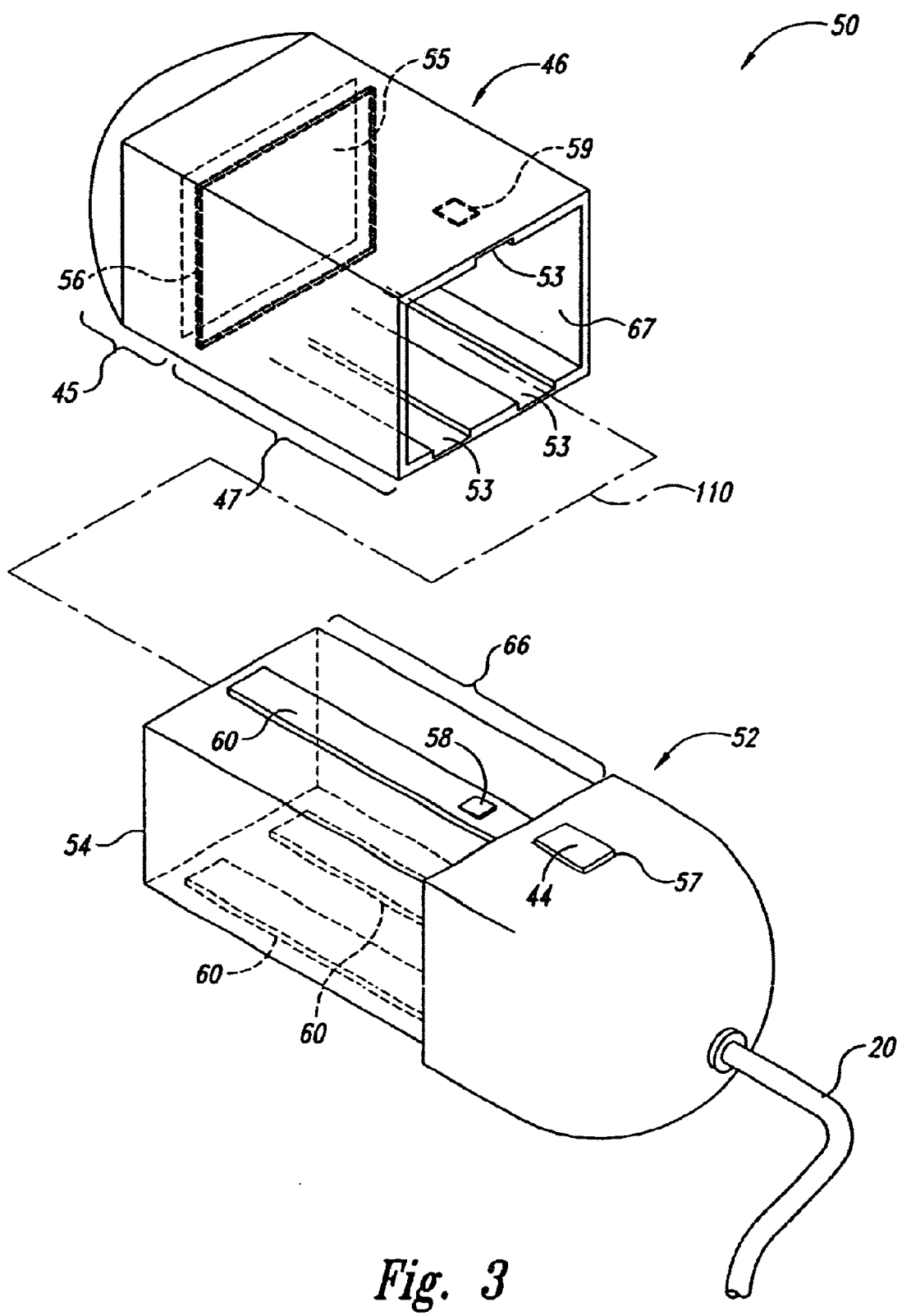
FIG. 3 is an isometric view of an ultrasonic scanhead assembly according to another embodiment of the invention.

FIG. 3 is an isometric view of a scanhead assembly 50 according to another embodiment of the invention. The scanhead assembly 50 is comprised of a frontal portion 46 and a rear portion 52, which may be joined as indicated by line 110. The frontal portion 46 is further comprised of an active section 45 that includes an ultrasonic array, impedance matching layers, a backing structure and a lens (not shown). Projecting rearwardly from the active section 45 is a skirt 47 that has an opening 67. The active section 45 also terminates at a connective interface 55 that is located within the skirt 47 and has a plurality of conductive elements (not shown in FIG. 3) positioned on it. The arrangement of the conductive elements on the connective interface 55 is shown in an additional figure, will be discussed in greater detail below. A sealing element 56 is positioned within the skirt 47 at a location adjacent to the interface 55 to prevent fluids or other contaminants from migrating onto the interface 55 when the frontal portion 46 and the rear portion 52 are mated. One or more guide grooves 53 are also located within the skirt 47 to guide the frontal portion 46 and the rear portion 52 into proper alignment when the portions 46 and 52 are slidably engaged. A non-symmetrical positioning of the grooves 53 assures that the frontal portion 46 and the rear portion 52 are in the proper relative orientation prior to mating.

Referring still to FIG. 3, the rear portion 52 has an elongated engagement portion 66 that is structured to be inserted into the opening 67 of the frontal portion 46. The rear portion 52 contains a beamformer (not shown) and includes a connective interface 54 at the end of the engagement portion 66 that has a plurality of conductive elements disposed thereon. The arrangement of the conductive elements on the connective interface 54 will also discussed below in greater detail in connection with another figure. The engagement portion 66 of the rear portion 52 may also include guide elements 60 that mesh with the guide grooves 53 in the skirt 47 when the frontal portion 46 and the rear portion 52 are slidably engaged. The rear portion 52 is also coupled to the scanhead cable 20. The cable 20 includes conductors to transfer a beamformed signals or data from the beamformer to the processor 33 (as shown in FIG. 2), in addition to conductors for transferring control signals and electrical power from the processor 33 to the scanhead assembly 50. The rear portion 52 also includes a latching mechanism 57 to lockably engage the rear portion 52 into the frontal portion 46 when the engagement portion 66 is fully inserted into the skirt 47. The locking mechanism includes a pawl 58 that is received by a recess 59 within the skirt 47. Once engaged, the latching mechanism 57 may be released by depressing a release 44.

Figure 4:
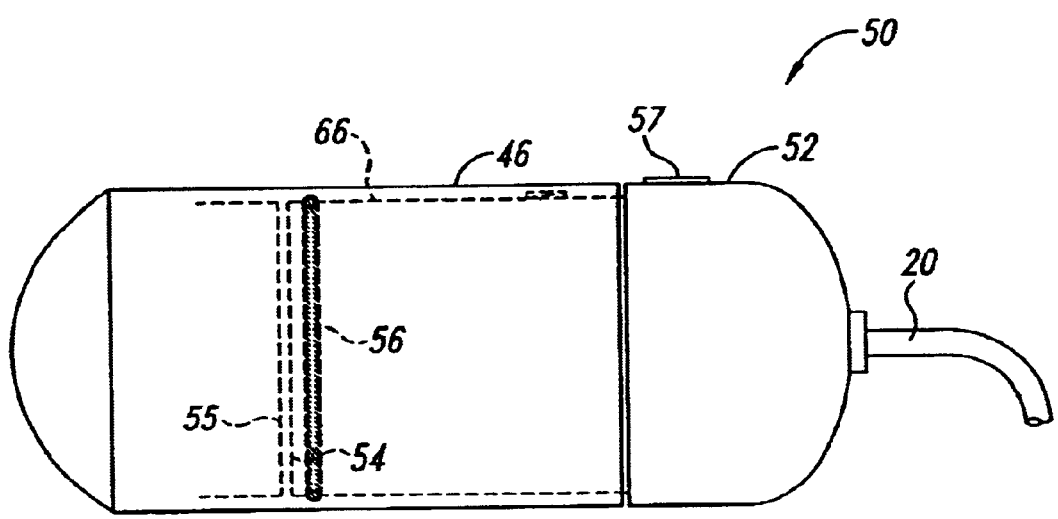
FIG. 4 is a plan view of an ultrasonic scanhead assembly according to another embodiment of the invention.

Turning now to FIG. 4, the scanhead assembly 50 is shown with the rear portion 52 slidably inserted into the frontal portion 46 so that the connective interface 54 of the rear portion 52 substantially abuts the connective interface 55 of the frontal portion 46, thus permitting electrical coupling between the frontal portion 46 and the rear portion 52. The sealing element 56 is compressed between the frontal portion 46 and the engagement portion 66 of the rear portion 52 to achieve a liquid tight seal in the proximity of the interfaces 54 and 55. The sealing element may be an elastomeric sealing device, such as an elastomeric o-ring, although other alternatives exist.

Figure 5:
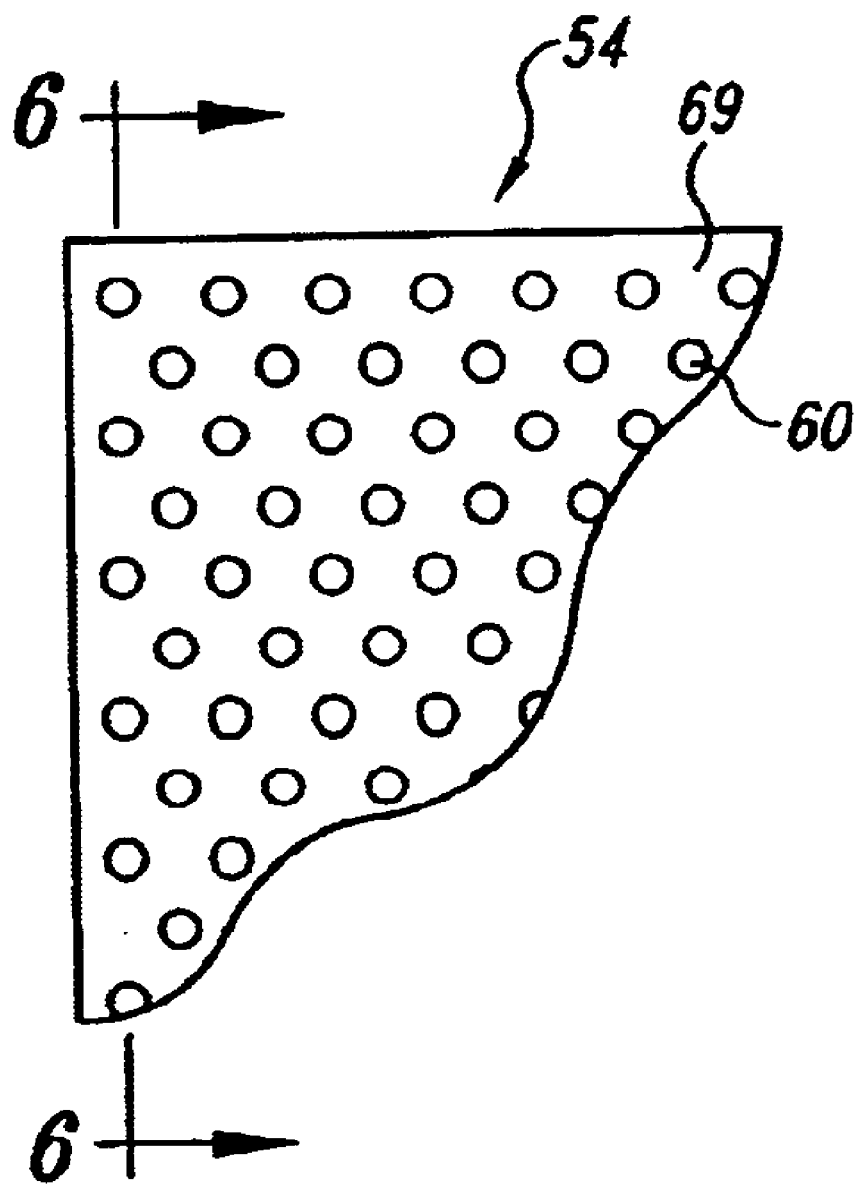
FIG. 5 is a partial plan view of a portion of an ultrasonic scanhead assembly according to another embodiment of the invention.

FIG. 5 shows a partial plan view of the connective interface 54. The connective interface 54 is comprised of a plurality of conductive members 60 that are disposed on a dielectric support member 69. Although the members 60 as shown in FIG. 5 are arranged in a staggered pattern, other alternative arrangements of the members 60 are possible. For example, rectangular, or even concentric circular patterns may be used.

Figure 6:
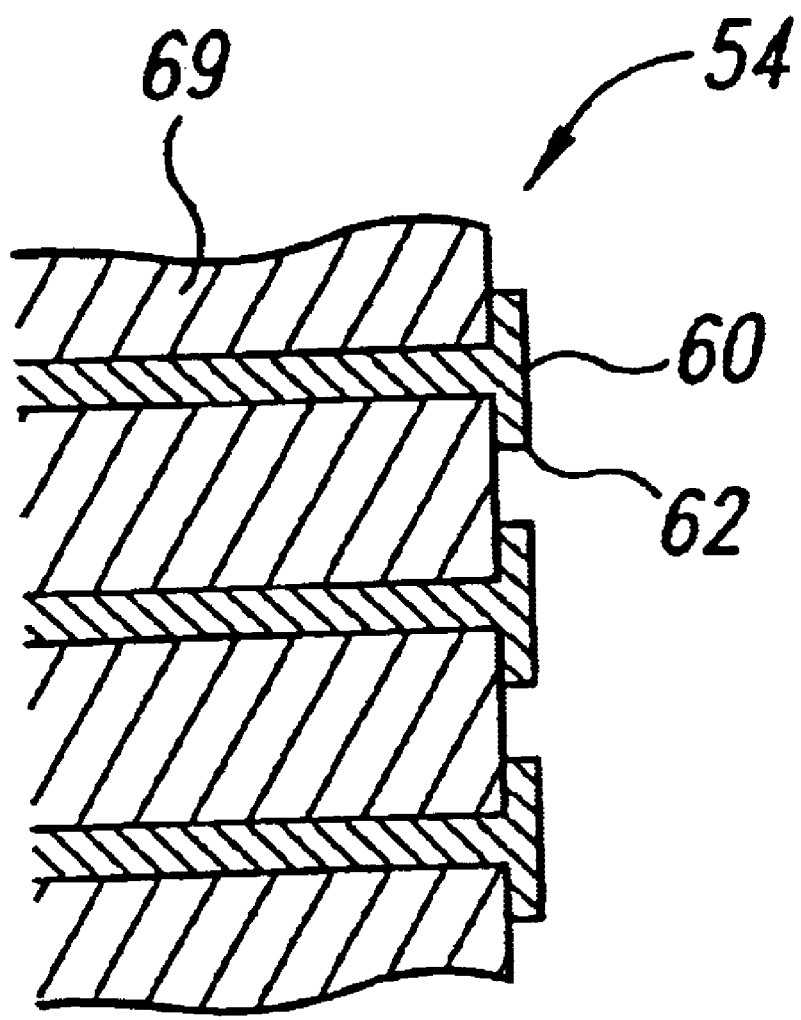
FIG. 6 is a partial cross sectional view of a portion of an ultrasonic scanhead assembly according to another embodiment of the invention.

FIG. 6 shows a partial sectional view of interface 54 in the direction 6—6 of FIG. 5. The members 60 are mutually spaced apart and project into a dielectric support member 69 to electrically couple with the beamformer (not shown) located within the rear portion 52. The members 60 may have a relatively flat engagement face 62 that extends outwardly from the dielectric support member 69, or alternatively, the members may be flush mounted to the support member 69.

Figure 7:
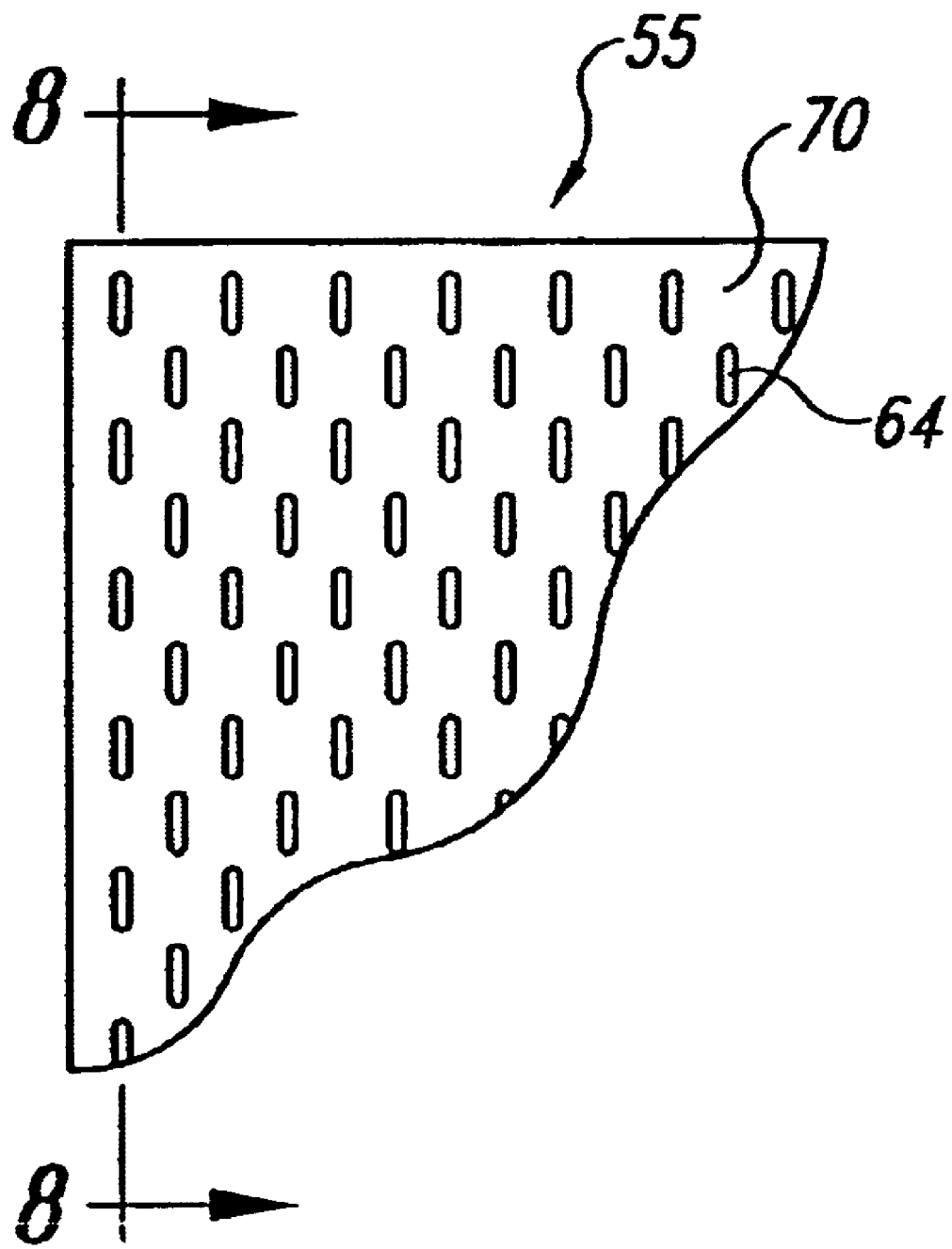
FIG. 7 is a partial plan view of another portion of an ultrasonic scanhead assembly according to another embodiment of the invention.

Referring now to FIG. 7, a partial plan view of the connective interface 55 is shown. The interface 55 is comprised of a plurality of conductive members 64 that are disposed on a dielectric support member 70 that project into the member 70 to electrically couple with the piezoelectric elements of the transducer assembly (not shown) located in the active section 45 of the frontal portion 46 (as shown in FIG. 3). The members 64 are arranged on the member 70 in the same pattern as the conductive elements 60 on the interface 54, so that contact between the members 60 and 64 occurs when the frontal portion 46 is mated to the rear portion 52. The members 64 are structured to provide a bias to permit the members 64 to springably engage the members 60 when the portion 46 is mated to the portion 52.

Figure 8:
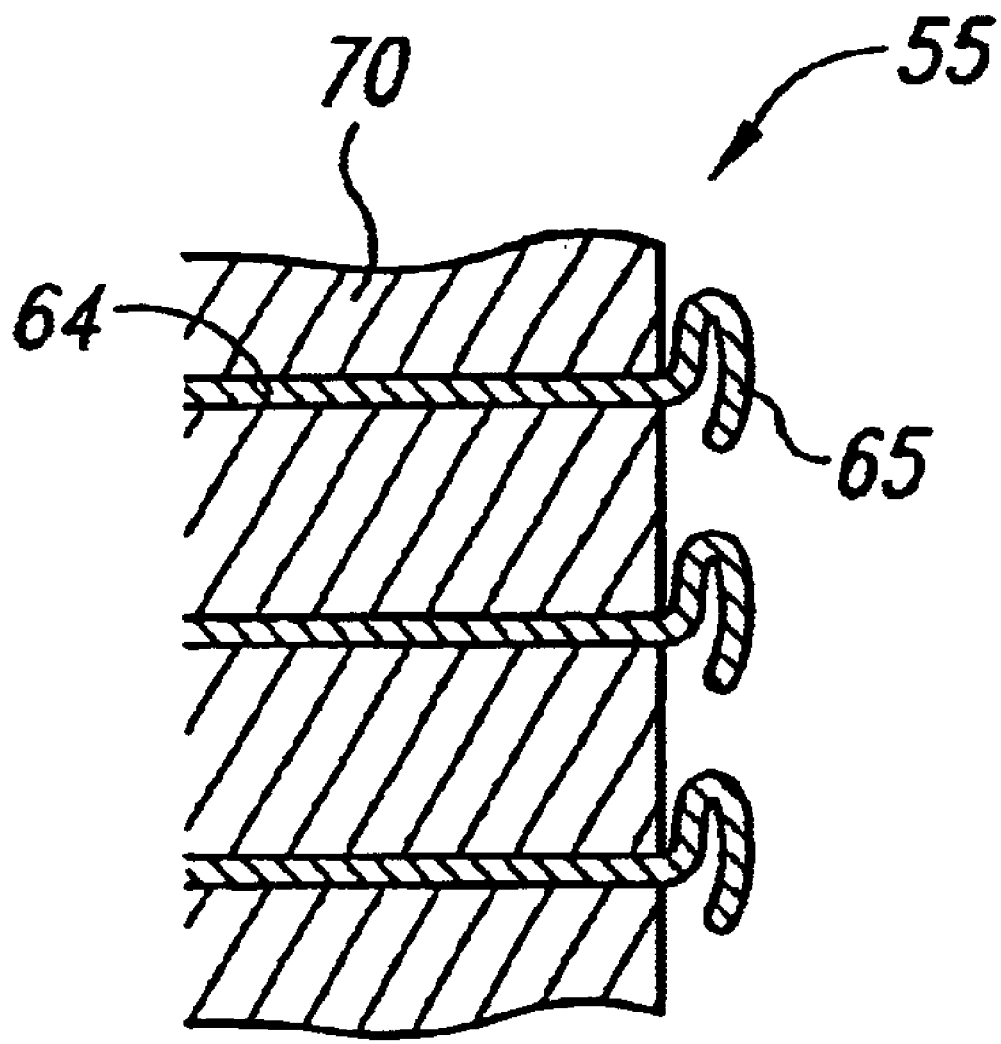
FIG. 8 is a partial cross sectional view of another portion of an ultrasonic scanhead assembly according to another embodiment of the invention.

FIG. 8 shows a partial sectional view of the interface 55 in the direction 8—8 of FIG. 7. The members 64 are mutually spaced apart and supported within a dielectric support member 70, having a spring end 65 that is biased outwardly from the surface of the dielectric support member 70. The spring end 65 may therefore be springably compressed to maintain electrical continuity between member 64 and member 60 (as shown in FIGS. 5 and 7) when the members 60 and 64 are brought into contact.

Figure 9:
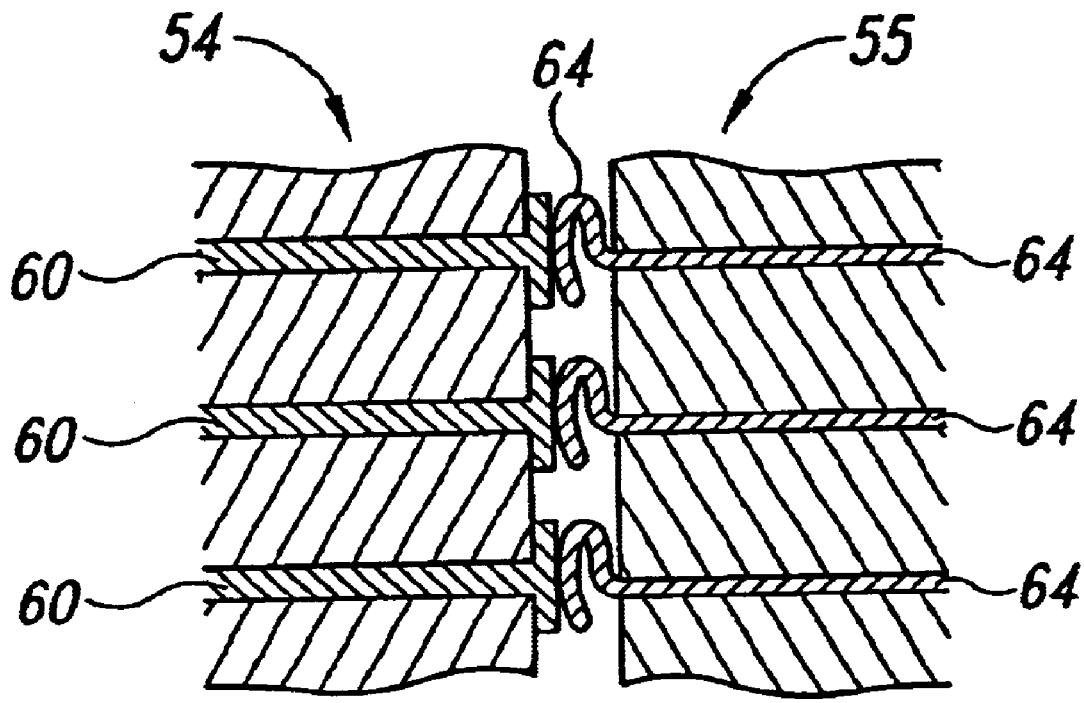
FIG. 9 is a partial cross sectional view of mating portions of an ultrasonic scanhead assembly according to another embodiment of the invention.

FIG. 9 shows a partial cross sectional view of the interfaces 54 and 55 when the members 60 and 64 are brought into contact. The bias provided in spring end 65 of the member 64 advantageously allows the members 60 and 64 to maintain electrical contact even if the interfaces 54 and 55 are subject to a relative mechanical misalignment, or are slightly displaced apart. The members 64 may be fabricated from beryllium copper in order to attain high elasticity, although other materials may be used. In addition, the spring end 65 of member 64 and the flat engagement face 62 of member 54 may be plated with gold, or similar metals to prevent surface oxidation.

Numerous features are present in the foregoing embodiment. Referring again to FIGS. 3 and 4, an important feature of the foregoing embodiment is a beamformer that is advantageously positioned in the rear portion 52, allowing the signal processing associated with beamforming to be at least partially performed in the scanhead assembly 50. The number of coaxial lines in the scanhead cable 20 may therefore be significantly reduced in comparison with other prior art scanhead cables, as previously described. An additional feature of the foregoing embodiment is that the frontal portion 54, which contains the transducer array, may be easily removed from the rear portion 52 in the clinical environment, which advantageously allows a number of different transducer configurations to be used by a common rear portion 52. Since a significant portion of the cost associated with the scanhead assembly 50 and the scanhead cable 20 resides in the beamformer and the cable, the ability to use the rear portion 52 with a variety of transducer configurations constitutes a significant cost savings. Further, in the event that a portion, or possibly all, of the active elements in the transducer assembly fail, a replacement frontal portion 46 may be easily positioned on the existing rear portion 52 to restore the scanhead assembly 50 to normal operation, thus avoiding the significant additional cost associated with replacing the entire scanhead assembly. Still another feature of the foregoing embodiment is that the connective interface 55, which has conductive members 64 having spring ends 65, as shown in FIGS. 7 and 8, is deeply recessed within the frontal portion 46 and protected by a skirt 47 that protects the relatively delicate spring ends 65 from physical damage. The skirt 47 also protects the connective interface 55 from contamination by various substances commonly used in ultrasound procedures, such as coupling gels. Although the connective interface 54 has exposed conductive members, they are generally flat, or even flush-mounted structures, which are inherently less susceptible to physical damage, and more easily cleaned if contaminated. Finally, as best seen in FIG. 4, the previously described embodiment advantageously includes an elastomeric seal element 56 to prevent liquids, such as sterilants, from migrating into and between the interfaces 54 and 55 when the frontal portion 46 and the rear portion 52 are mated.

Figure 10:
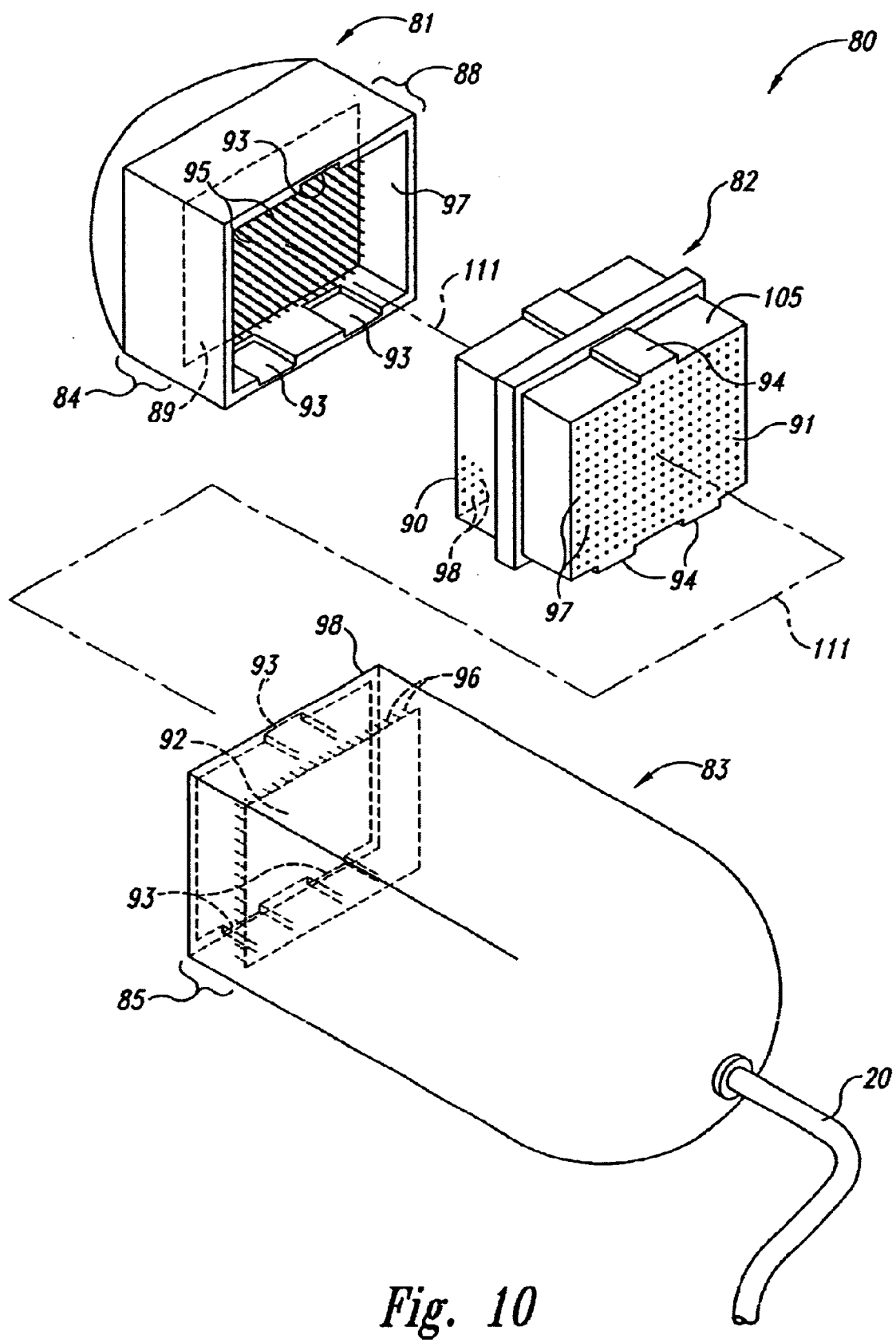
FIG. 10 is an isometric view of an ultrasonic scanhead assembly according to still another embodiment of the invention.

FIG. 10 is an isometric view of a scanhead assembly 80 according to still another embodiment of the invention. The scanhead assembly 80 includes a frontal portion 81, an interposer portion 82, and a rear portion 83 that may be joined as indicated by line 111. The frontal portion 81 has an active section 84 that contains the transducer assembly, impedance matching layers, the acoustic backing layer and lens. The active section 84 terminates at a connective interface 89 that contains a plurality of conductive pins 95 extending outwardly from the connective interface 89 that are electrically coupled to the elements of the transducer assembly in the active section 84. The conductive pins 95 are comprised of copper that has been electroplated with gold, although other alternatives exist. A skirt 88 extends rearwardly from the connective interface 89 to an opening 97 that receives the interposer portion 82. Guide grooves 93 are disposed on the inner surface of the skirt 88 to allow the interposer portion 82 to be properly aligned within the opening 97 when the frontal portion 81 and the interposer portion 82 are mated.

The rear portion 83 of the scanhead assembly 80 includes a connective interface 92 having a plurality of conductive pins 96 extending outwardly from the interface 92. The conductive pins 96 are comprised of copper that has been electroplated with gold, although other alternatives exist. A skirt 85 extends forwardly from the interface 92 to an opening 98 that receives the interposer portion 82. The conductive pins 96 of connective interface 92 are electrically coupled to a beamformer (not shown), which is located within the rear portion 83. The beamformer is further electrically coupled to a scanhead cable 20 that includes conductors to transfer beamformed signals or data from the beamformer to the processor 33 (as shown in FIG. 3), and also includes conductors for transferring control signals and electrical power from the processor 33 to the scanhead assembly 80. Guide grooves 93 are disposed on the inner surface of the skirt 85 to allow the interposer portion 82 to be properly aligned when the rear portion 83 and the interposer portion 82 are mated.

Still referring to FIG. 10, the interposer portion 82 is further comprised of a body 105 that is fabricated from a generally rigid, dielectric polymer, such as NYLON® or DELRIN®, although other suitable materials exist. The interposer portion 82 also includes a connection interface 90 and an opposing connection interface 91. The connection interface 90 has a plurality of pin receivers 98 that are positioned within the connective interface 90 that are electrically coupled to a plurality of pin receivers 97 on the connective interface 91. The pin receivers 98 on interface 90 engageably receive the pins 95 on the interface 89 when the frontal portion 81 and the interposer portion 82 are mated. Similarly, the pin receivers 97 on the interface 91 engageably receive the pins 96 on the interface 92 when the interposer portion 82 is mated with the rear portion 83. The connective interfaces 90 and 91 further include sealing layers, which will be discussed in further detail in connection with another figure. The interposer portion 82 further includes guide members 94 that mesh with the guide grooves 93 in the frontal portion 81 and the rear portion 83 to allow the portions 80 and 83 to properly align with the interposer 82.

Figure 11:
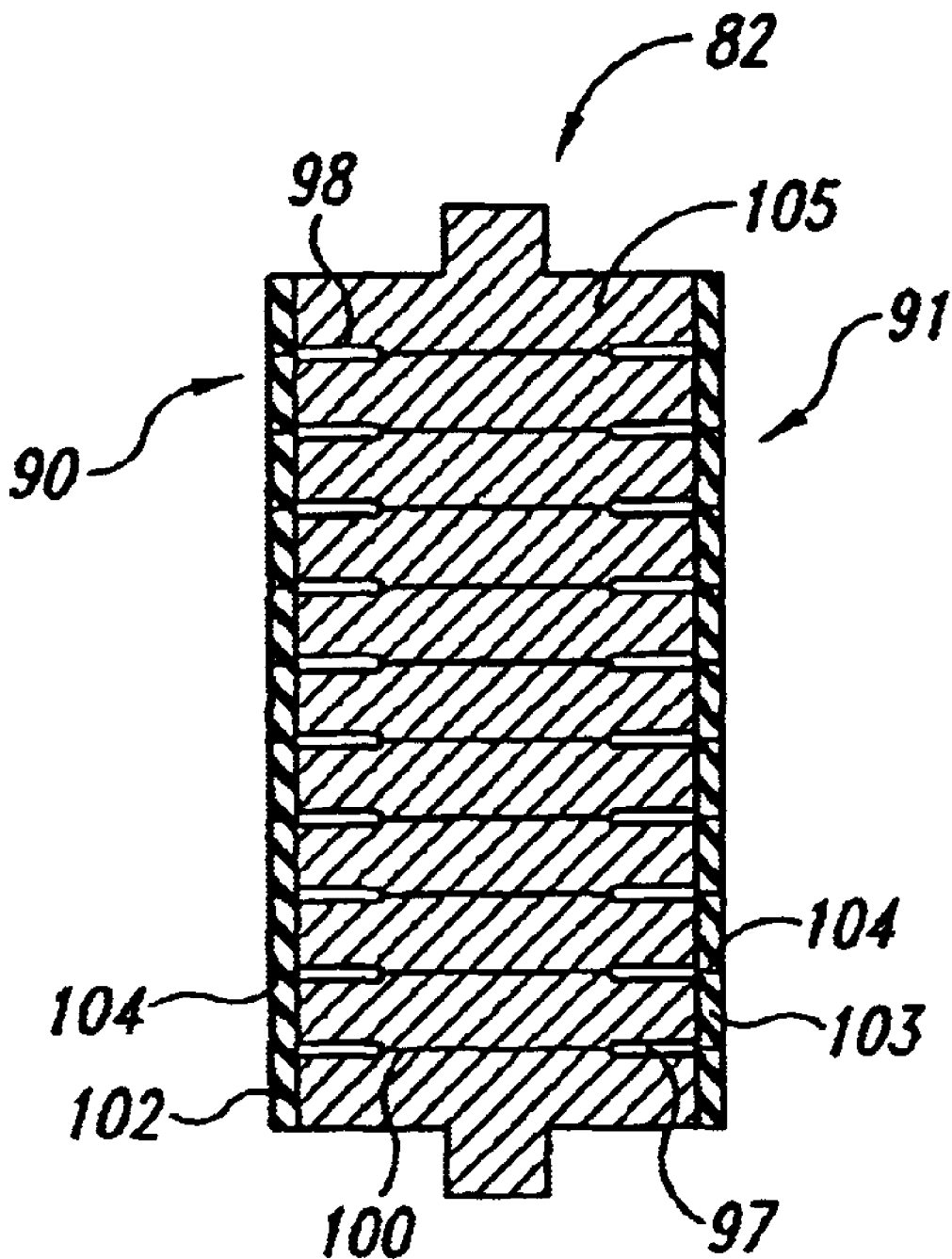
FIG. 11 is a cross sectional view of a portion of an ultrasonic scanhead assembly according to still another embodiment of the invention.

FIG. 11 is a cross sectional view of the interposer portion 82 that shows a sealing layer 102 disposed on the connective interface 90, and a similar sealing layer 103 disposed on the opposing interface 91. The sealing layers are comprised of a flexible and resilient material, such as synthetic rubber, although other alternative materials exist. The sealing layers 102 and 103 each have a plurality of perforations 104 that project through the sealing layers 102 and 103 that generally concentrically coincide with the position of the pin receivers 97 and 98. The perforations 104 have a diameter that is smaller than the pins 95 and 96 (as shown in FIG. 10) so that a compressive and fluid-restrictive seal is formed around each of the pins when the interposer portion 82 is mated to the frontal section 81 and the rear section 83. The interposer portion 82 also includes the conductors 100 that project through the body 105 to connect the pin receivers 97 with the pin receivers 98.

Figure 12:
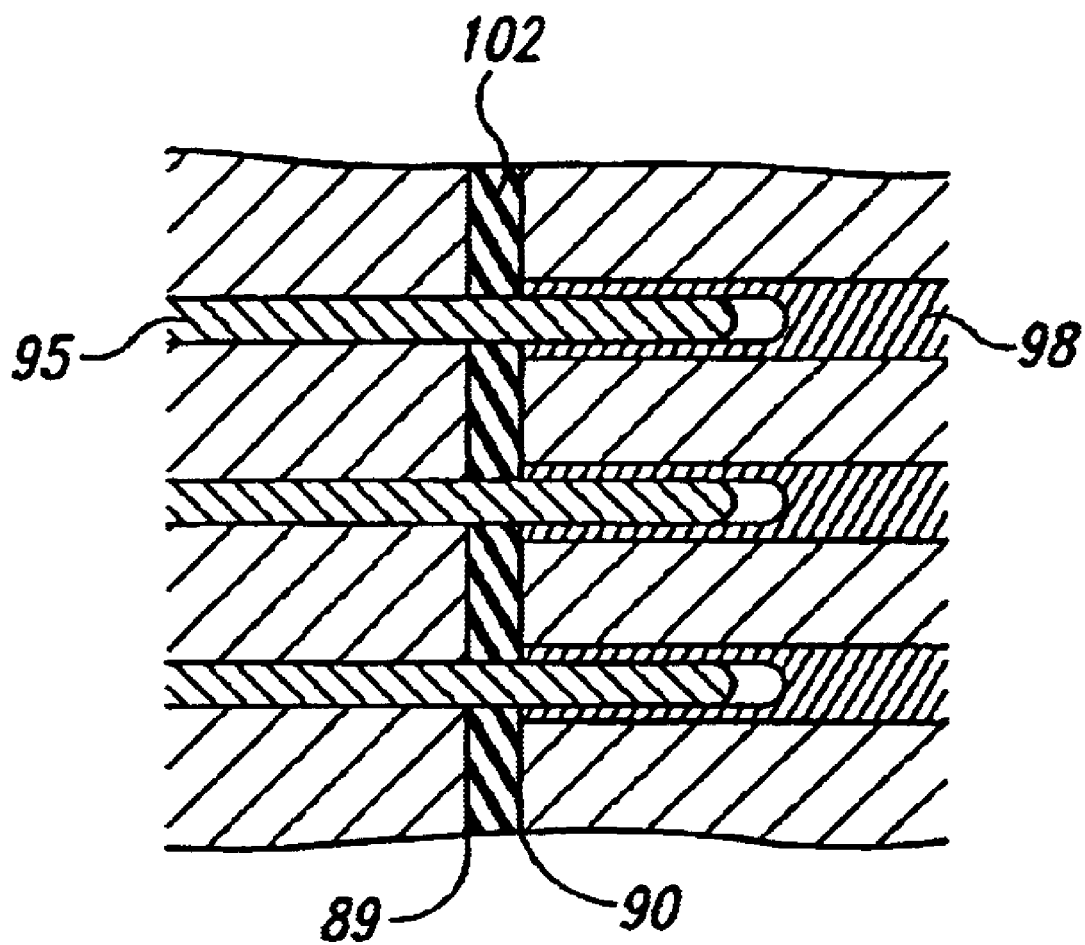
FIG. 12 is a partial cross sectional view of mating portions of an ultrasonic scanhead assembly according to still another embodiment of the invention.

FIG. 12 is a partial cross sectional view of the connective interface 89 of the frontal portion 81 mated with the connective interface 90 of the interposer portion 82. When pins 95 are received by the pin receivers 98, as shown, the sealing layer 102 is positioned between the interfaces 89 and 90, and compressively surrounds the pins 95 to prevent the migration of fluids into the electrical connection formed between pins 95 and receivers 98. The sealing layer 102 also advantageously provides a wiping action that removes contaminants that may exist on the pins 95 prior to insertion in the receivers 98. Although FIG. 12 has shown a cross sectional detail of interfaces 89 and 90 when they are mated, the description above applies equally to the mating of interfaces 91 and 92, as shown in FIG. 10.

Additional advantageous features are present in the foregoing embodiment. For example, referring to FIG. 10, an interposer portion 82 that has conductive interfaces 90 and 91 that project into the frontal portion 81 and rear portion 83 allows the pins 95 and pins 96 to be recessed within the frontal portion 81 and rear portion 83, respectively, thus protecting the pins 95 and 96 from physical damage. With reference to FIGS. 11 and 12, the sealing layers 102 and 103 advantageously provide a fluid-tight seal to be maintained around the pins 95 and 96 when the portions 81 and 83 are mated with the interposer 82. As a result, the scanhead assembly is less susceptible to malfunctions caused by exposure to liquids. Still referring to FIGS. 11 and 12, the layers 102 and 103 also allow the pins 95 and 96 to be wiped with each insertion, so that contaminant are wiped off the pins. Additionally, since the interposer portion 82 is relatively inexpensive to manufacture, it may be discarded, and replaced by a new interposer portion 82 if the interposer portion malfunctions due to a damaged receiver, or for other reasons.

Figure 13:
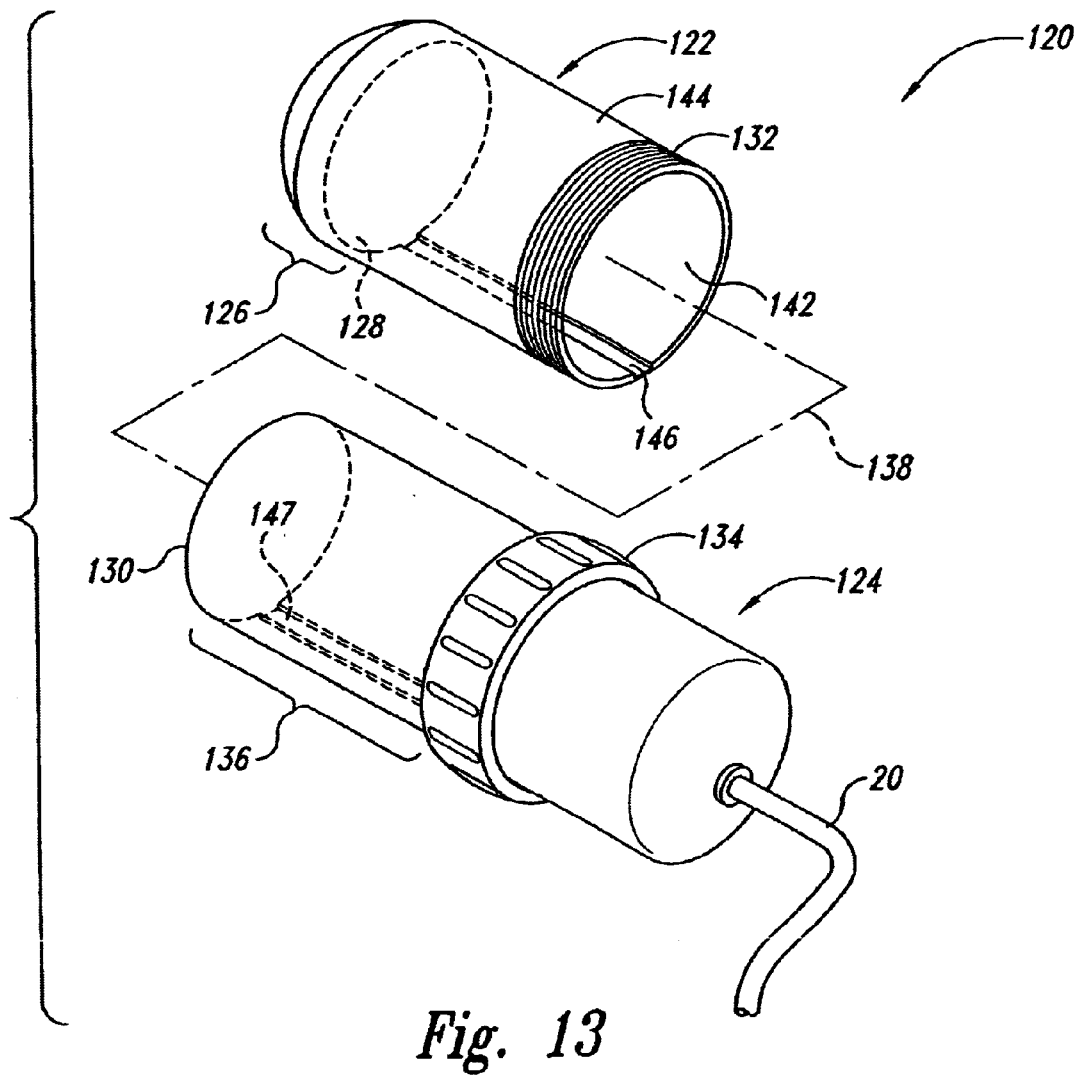
FIG. 13 is an isometric view of an ultrasonic scanhead assembly according to yet another embodiment of the invention.

FIG. 13 is an isometric view of a scanhead assembly 120 according to yet another embodiment of the invention. The scanhead assembly 120 is generally axisymmetric in shape, and includes a frontal portion 122, and a rear portion 124, which may be joined as indicated by line 138. The frontal portion 122 has an active section 126 that contains the transducer assembly, impedance matching layers, the acoustic backing layer and lens (not shown). Projecting rearwardly from the active section 126 is a skirt 144 that terminates at an open end 142. The frontal portion 122 also includes a threaded portion 132 that is disposed on the skirt 144 opposite the active section 126. The active section 126 also terminates at a connective interface 128 that is located within the skirt 144 and has a plurality of conductive elements disposed on the interface 128 that are electrically coupled to the transducer assembly in the active section 126. The conductive elements on the connective interface 130 are preferably the conductive members 64 having an elastic bias, as shown in FIG. 7, but may include other conductive elements of various shapes and configurations.

Referring still to FIG. 13, the rear portion 124 has an elongated engagement portion 136 that is structured to be inserted into the opening 142 of the frontal portion 122. A collar 134 having internal threads (not shown) is positioned on the rear portion 124 to threadably engage the threaded portion 132 on the frontal portion 122 when the frontal portion 122 and the rear portion 124 are mated. As in the previous embodiments, the rear portion 124 also contains a beamformer (not shown) and includes a connective interface 130 at the end of the engagement portion 136 that has a plurality of conductive elements disposed on the interface 130 that are electrically coupled to the beamformer within the rear section 124. The conductive elements are preferably the connective members 60 as shown in FIG. 6, but other configurations may be used also. The engagement portion 136 also includes guide groove 146 that meshes with the guide element 147 on the engagement portion 136 when the frontal portion 122 and the rear portion 124 are slidably engaged. The rear portion 124 is also coupled to a scanhead cable 20 that is further connected to the processor 33 (as shown in FIG. 2).

Figure 14:
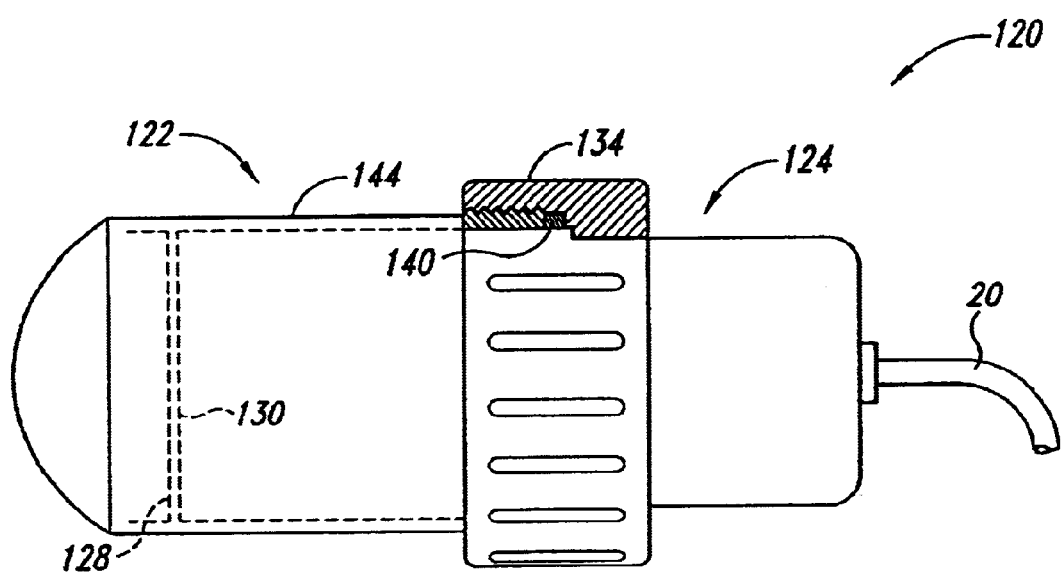
FIG. 14 is a plan view of an ultrasonic scanhead assembly according to yet another embodiment of the invention.

Turning now to FIG. 14, the scanhead assembly 120 is shown with the rear portion 124 slidably inserted into the frontal portion 122 so that the connective interface 130 of the rear portion 124 substantially abuts the connective interface 128 of the frontal portion 122 to establish electrical coupling between the frontal portion 122 and the rear portion 124. A sealing element 140 is compressed between the skirt 144 and the collar 134 to achieve a liquid tight seal. The sealing element 140 may be comprised of a synthetic rubber, such as neoprene, although other alternatives exist.

The previously described embodiment possesses many of the features present in other embodiments, and further advantageously allows the two mating portions of the scanhead assembly to be threadably mated to compress an elastomeric sealing member. As a result, the previously described embodiment provides a liquid tight seal that provides still further protection from the in-migration of fluids.

The above description of illustrated embodiments of the invention is not intended to be exhaustive or to limit the invention to the precise form disclosed. While specific embodiments of, and examples of, the invention are described in the foregoing for illustrative purposes, various equivalent modifications are possible within the scope of the invention, as those skilled within the relevant art will recognize. Moreover, the various embodiments described above can be combined to provide further embodiments. Accordingly, the invention is not limited by the disclosure, but instead the scope of the invention is to be determined entirely by the following claims.

What is claimed is:

1. An ultrasonic imaging system, comprising:
   an ultrasonic scanhead assembly having a frontal portion and a removably attached rear portion, wherein the frontal portion further includes an active section capable of transmitting and receiving signals at ultrasonic frequencies, and the rear portion further includes a beamformer capable of dynamically focusing at least a portion of the ultrasonic signals transmitted or received by the active section, the frontal portion and the rear portion being electrically coupled when removably attached, the beamformer being substantially enclosed within the rear portion when the frontal portion and the rear portion are detached;
   an ultrasonic processor to exchange signals with the rear portion of the ultrasonic scanhead assembly and process the signals received from the beamformer to produce a visual image; and
   a scanhead cable coupling the scanhead assembly to the ultrasonic processor.

2. The ultrasonic imaging system according to claim 1, wherein the frontal portion is further comprised of a first connective interface electrically coupled to the active section, and the rear portion is further comprised of a second connective interface electrically coupled to the beamformer, the first interface abutting the second interface when the frontal portion and the rear portions are removably attached to establish electrical coupling therebetween.

3. The ultrasonic imaging system according to claim 2, wherein the first connective interface comprises a plurality of first conductive elements and the second connective interface comprises a plurality of second conductive elements, the first conductive elements being in corresponding opposition to the second conductive elements, wherein the first conductive elements substantially contact the second conductive elements when the frontal portion and the rear portion are removably attached.

4. The ultrasonic imaging system according to claim 3, wherein the plurality of first conductive elements are engageably received by the plurality of second conductive elements.

5. The ultrasonic imaging system according to claim 3, wherein the plurality of second conductive elements are engageably received by the plurality of first conductive elements.

6. The ultrasonic imaging system according to claim 3, wherein the plurality of first conductive elements are comprised of a plurality of members having an end portion with a springable bias.

7. The ultrasonic imaging system according to claim 3, wherein the plurality of second conductive elements are comprised of a plurality of members having an approximately flat end portion.

8. The ultrasonic imaging system according to claim 1, wherein the scanhead cable is further comprised of at least one coaxial line to couple the beamformer to the processor.

9. The ultrasonic imaging system according to claim 1, wherein the scanhead cable is further comprised of at least one conductor capable of coupling control signals between the scanhead assembly and the processor.

10. The ultrasonic imaging system according to claim 1, wherein the processor is further comprised of an image processor capable of receiving signals from the beamformer and generating visual image data therefrom.

11. The ultrasonic imaging system according to claim 10, wherein the processor is further comprised of a system controller coupled to the image processor and the beamformer.

12. The ultrasonic imaging system of claim 1, wherein the active section is further comprised of a transducer array having an emission surface and an opposed surface, the emission surface having at least one impedance matching layer fixedly attached thereto, and the opposed surface has a backing layer that is fixedly attached thereto.

13. The ultrasonic imaging system of claim 12, wherein the transducer array is a linear array.

14. The ultrasonic imaging system of claim 12, wherein the transducer array is a two dimensional array.

15. The ultrasonic imaging system of claim 12, wherein the active section is further comprised of a lens.

16. A scanhead assembly for a ultrasonic imaging system, comprising:
 a first portion having a frontally positioned active section and a rearwardly positioned first connective interface that is electrically coupled to the active section; and
 a second portion having a frontally positioned second connective interface that is electrically coupled to a beamformer positioned within the second portion, the first and second portions being structured to be removably attached to provide an electrical coupling between the active region and the beamformer when the first and second connective interfaces are engaged, the beamformer being substantially enclosed within the second portion when the first portion and the second portion are separated.

17. The scanhead assembly according to claim 16, wherein the first connective interface is further comprised of a plurality of first conductive elements and the second connective interface is further comprised of a plurality of second conductive elements, the first elements on the first interface being in corresponding opposition to the second elements on the second interface, the first conductive elements on the first interface substantially contacting the second conductive elements on the second interface when the first and second portions are removably attached.

18. The scanhead assembly according to claim 17, wherein the first conductive elements and the second conductive elements are further comprised of axisymmetric pins.

19. The scanhead assembly according to claim 17, wherein the first conductive elements are further comprised of elements having ends with an elastic bias structured to be compressed when contacted by the second conductive elements.

20. The scanhead assembly according to claim 17, wherein the second conductive elements are further comprised of elements with an approximately flat engagement portion for contacting the first conductive elements.

21. The scanhead assembly according to claim 16, wherein the first portion is further comprised of a skirt section extending rearwardly from the first connective interface to define an interior portion having an opening, and the second portion is further comprised of an engagement portion extending rearwardly from the second connective interface, the engagement portion being structured to be received by the opening and slidably inserted into the interior portion.

22. The scanhead assembly according to claim 21, wherein the first portion is further comprised of at least one sealing element positioned with the interior portion of the skirt section to form a fluid tight space enclosing the first and second connective interfaces when the first and second portions are removably attached.

23. The scanhead assembly according to claim 21, wherein the second portion is further comprised of at least one sealing element positioned on the engagement portion to form a fluid tight space enclosing the first and second connective interfaces when the first and second portions are removably attached.

24. The scanhead assembly according to claim 21, wherein the rear portion is further comprised of a latching mechanism to latchably engage the second portion to the first portion when the first and second portions are removably attached.

25. The scanhead assembly according to claim 21, wherein the engagement portion is further comprised of at least one first guide element extending at least partially along the length of the engagement portion, and the skirt section is further comprised of at least one second guide element in corresponding opposition to the first guide element, the first guide element and the second guide element being structured to be meshably engaged when the engagement portion is inserted in the skirt portion.

26. The scanhead assembly according to claim 25, wherein the skirt section is further comprised of a threaded portion disposed on the skirt section and adjacent to the opening, and the rear portion is further comprised of a collar structured to be threadably engaged with the threaded portion to demountably couple the first portion to the second portion.

27. The scanhead assembly according to claim 26, further comprising a sealing element positioned between the skirt section and the rear portion.

28. The scanhead assembly according to claim 16, wherein the second portion is further comprised of a scanhead cable coupled to the beamformer.

29. A scanhead assembly for a ultrasonic imaging system, comprising:
- a first portion having a frontally positioned active section that is electrically coupled to a first connective interface;
- a second portion having an internally positioned beamformer that is electrically coupled to a second connective interface; and
- an interposer portion having a first end structured to be received by the first connective interface on the first portion, and an opposed second end structured to be received by the second connective interface on the second portion, the interposer portion electrically coupling the active region in the first portion to the beamformer in the second portion when the first and second portions are coupled to the interposer and wherein the beamformer is substantially enclosed in the second portion when the second portion is decoupled from the interposer.

30. The scanhead assembly according to claim 29, wherein the first connective interface on the first portion is further comprised of a plurality of first conductive elements, and the second connective interface on the second portion is further comprised of a plurality of second conductive elements, the second conductive elements being in corresponding opposition to the first conductive elements.

31. The scanhead assembly according to claim 30, wherein the interposer portion is further comprised of a plurality of conductors extending through the interposer portion from the first end to the second end, each conductor further having a first terminal end disposed on the first end to engageably contact the first conductive elements on the first connective interface, and a second terminal end disposed on the second end to engageably contact the second conductive elements on the second connective interface.

32. The scanhead assembly according to claim 29, wherein the interposer is further comprised of a first sealing element disposed on the first end, and a second sealing element disposed on the second end, the first sealing element being positioned between the first connective interface and the first end when the first portion and the interposer portion are coupled, and the second sealing element being positioned between the second connective interface and the second end when the second portion and the interposer portion are coupled.

33. The scanhead assembly according to claim 30, wherein the first conductive elements and the second conductive elements are comprised of axisymmetric pins.

34. The scanhead assembly according to claim 29, wherein the second portion is further comprised of a scanhead cable coupled to the beamformer.

35. A method of performing an ultrasound diagnostic procedure on a patient, comprising:
- selecting a first scanhead portion containing an ultrasonic transducer capable of transmitting ultrasonic energy and receiving ultrasonic echoes;
- removably attaching the first scanhead portion to a second scanhead portion containing a beamformer capable of dynamically focusing the ultrasonic signals and ultrasonic echoes, the beamformer being substantially enclosed within the second scanhead portion when the second scanhead portion is separated from the first scanhead portion;
- placing the removably attached first and second portions against the skin of the patient;
- projecting ultrasonic energy into the body of the patient; and
- receiving ultrasonic echoes from an interior portion of the body.

36. The method according to claim 35, wherein the act of selecting a first scanhead portion is further comprised of selecting a first scanhead portion having a linear transducer array.

37. The method according to claim 35, wherein the act of selecting a first scanhead portion is further comprised of selecting a first scanhead portion having a two-dimensional transducer array.

38. The method according to claim 35, wherein the act of projecting ultrasonic energy into the body of the patient is further comprised of dynamically focusing the ultrasonic energy to a focal point within the body with the beamformer.

39. The method according to claim 35, wherein the act of receiving ultrasonic echoes from an interior portion of the body is further comprised of dynamically focusing the echoes received from the body of the patient to coincide with a focal point within the body with the beamformer.

40. The method according to claim 35, wherein the act of mating the first scanhead portion to a second scanhead portion is further comprised of coupling the removably attached portions to a processor using a scanhead cable.

41. The method according to claim 40, wherein the act of coupling the removably attached portions to a processor using a scanhead cable is further comprised of transmitting beamformed signals from the scanhead to the processor.

* * * * *